(12) United States Patent  (10) Patent No.: US 8,152,520 B2
Kooiman  (45) Date of Patent: Apr. 10, 2012

(54) ORTHODONTIC BRACKET AND USE THEREOF

(76) Inventor: Johan Anton Kooiman, Reeuwijk (NL)

( * ) Notice: Subject to any disclaimer, the term of this patent is extended or adjusted under 35 U.S.C. 154(b) by 250 days.

(21) Appl. No.: 12/445,249

(22) PCT Filed: Oct. 10, 2006

(86) PCT No.: PCT/NL2006/050254
§ 371 (c)(1),
(2), (4) Date: Apr. 10, 2009

(87) PCT Pub. No.: WO2008/044912
PCT Pub. Date: Apr. 17, 2008

(65) Prior Publication Data
US 2010/0021857 A1  Jan. 28, 2010

(51) Int. Cl.
A61C 5/00 (2006.01)
(52) U.S. Cl. .......................................... 433/17
(58) Field of Classification Search .............. 433/2–24
See application file for complete search history.

(56) References Cited

U.S. PATENT DOCUMENTS

| 4,350,487 | A | 9/1982 | Kesling et al. |
| 4,427,381 | A | 1/1984 | Hall |
| 5,993,207 | A | 11/1999 | Spencer |
| 6,139,317 | A | 10/2000 | Goldschmied |
| 2004/0072118 | A1 | 4/2004 | Heiser et al. |

OTHER PUBLICATIONS

International Search Report dated Jun. 13, 2007, from corresponding PCT application.

*Primary Examiner* — Cris L Rodriguez
*Assistant Examiner* — Mirayda A Aponte
(74) *Attorney, Agent, or Firm* — Young & Thompson

(57) ABSTRACT

A bracket for attaching an arch wire to a tooth includes a dental plate with a back and a front, wherein the back is intended to be attached to a tooth by an adhesive connection, and also an arch wire holder for fastening the arch wire to the bracket, wherein the arch wire holder is fitted at the front of the dental plate. The bracket farther includes an arm, a first end of which is attached, or can be attached, to the dental plate and a second end carries the arch wire holder. The arm extends along the front of the dental plate. The arm is made of bendable wire material, such that the position of the arch wire holder in respect of the dental plate can be adjusted by bending the arm. The invention further relates to the use of a bracket according to the invention.

17 Claims, 5 Drawing Sheets

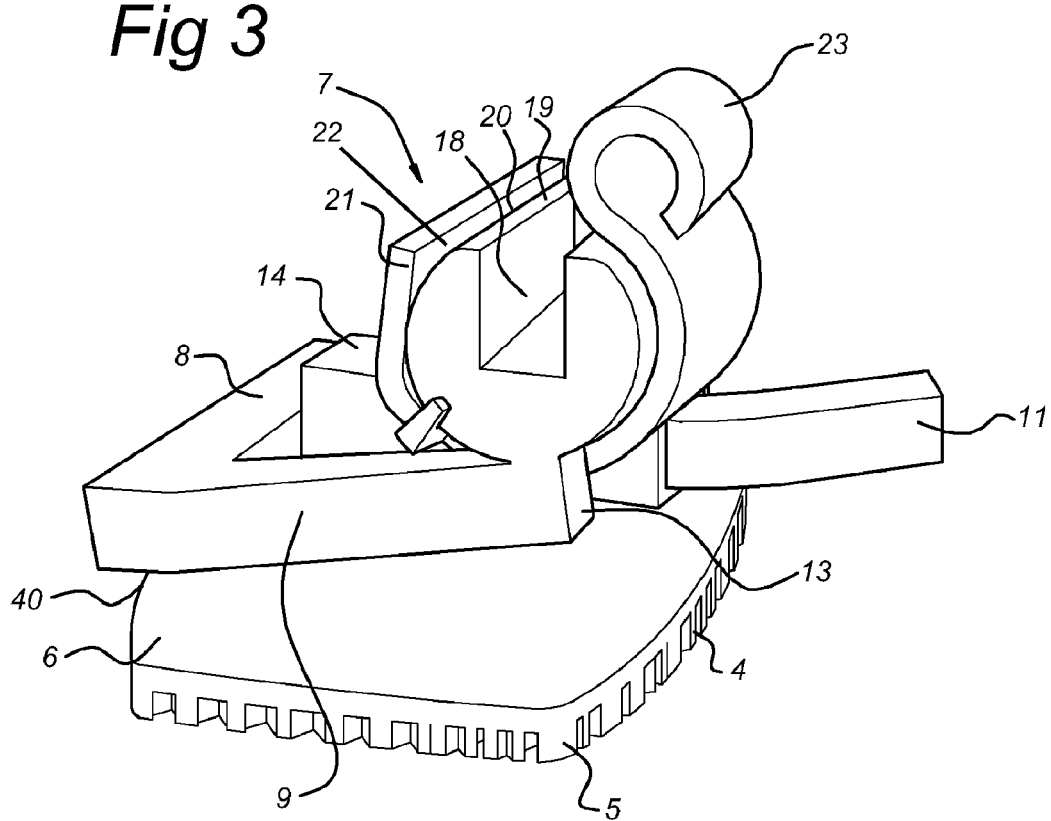

Fig 4a  Fig 4b  Fig 4c
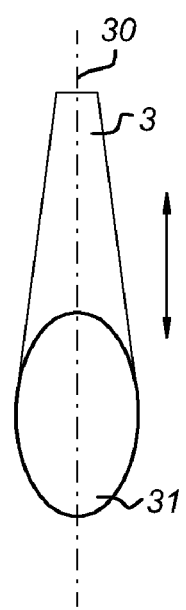
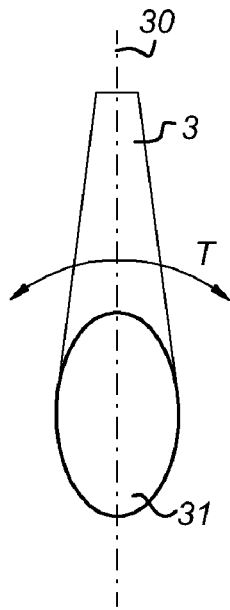
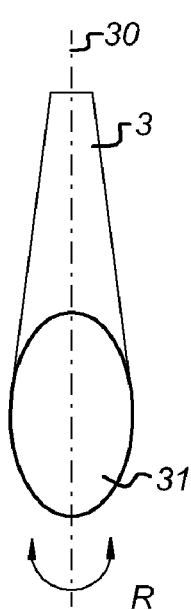
Fig 4d
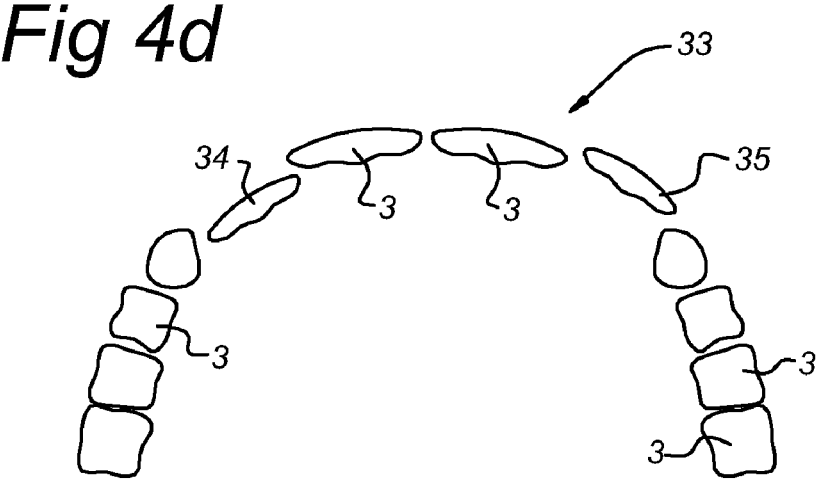

ORTHODONTIC BRACKET AND USE THEREOF

CROSS-REFERENCE TO RELATED APPLICATIONS

Are enumerated in the Application Data Sheet.

STATEMENT REGARDING FEDERALLY SPONSORED RESEARCH OR DEVELOPMENT

None.

THE NAMES OF THE PARTIES TO A JOINT RESEARCH AGREEMENT

None.

INCORPORATION-BY-REFERENCE OF MATERIAL SUBMITTED ON A COMPACT DISC

BACKGROUND OF THE INVENTION (1) Field of the Invention

The present invention belongs to the domain of orthodontics. The invention relates to a bracket for attaching an arch wire to a tooth, wherein the bracket comprises:

a dental plate with a back and a front, wherein the back is intended to be attached to a tooth by means of an adhesive connection and an arch wire for attaching the arch wire to the bracket, wherein the arch wire holder is fitted at the front of the dental plate.

(2) Description of Related Art

An arch wire is an arch-shaped wire which is placed on the outside along the tooth arch of the lower jaw or upper jaw, including in the case of orthodontic corrections. The arch wire is in this case attached to the teeth by so-called brackets. A bracket is generally constructed of a dental plate which is attached to a tooth by means of an adhesive connection. Mortars developed specifically for orthodontics or dental surgery are normally used for the adhesive connection. The dental plate is fitted with a holder with which the arch wire can be attached to the bracket. The way it is done is that the bracket is first attached to the teeth and then the arch wire is ligated, in other words fixed to the bracket. In so doing an effort is normally made to have the arch wire running as straight as possible—a so-called straight arch wire—this means that though the arch wire runs, just like the tooth arch, along an arch shape (for example more or less U-shaped), there has been no additional bending in respect of said arch shape, at any rate it is attempted as far as possible to avoid said additional bending in respect of the arch shape. However, practice shows that the brackets will not all be well aligned in respect of the arch wire, or else that in the course of the orthodontic treatment one or more brackets need to be adjusted in respect of the arch wire in order to exert a certain force on a tooth. In order to make this possible, there are substantially two solutions: the bracket is moved and/or the arch wire is additionally bent.

The disadvantage of moving the bracket is that it needs to be detached from the tooth and fixed to the tooth again, which is work-intensive. The additional bending of the arch wire is also work-intensive and, furthermore, is a task of precision. During additional bending of the arch wire there is, moreover, often a risk that, after additional bending in a particular zone of the arch wire, the arch wire also needs to be put back precisely into shape in other zones.

BRIEF SUMMARY OF THE INVENTION

The object of the present invention is to create a bracket according to the preamble of claim 1, which makes adjusting into a desired position of the arch wire holder in respect of the arch wire possible in a simple way.

The afore-mentioned object is achieved according to the invention in that the bracket further comprises an arm, a first end of which is attached, or can be attached, to the dental plate, and a second end carries the arch wire holder, in that the arm extends along the front of the dental plate and in that the arm is made of bendable wire material, such that the position of the arch wire holder in respect of the dental plate is adjustable by bending the arm. This prevents the bracket having to be detached from the tooth, if the arch wire is incorrectly positioned, for re-fixing thereof and also prevents the arch wire itself having to be additionally bent. This additional bending is work-intensive and, since several arch wires are needed for each orthodontic treatment, the additional bending has to be carried out several times at the same place in the teeth. According to the invention the adjustment is possible by attaching the arch wire holder to the free end of an overhanging arm, which is attached, or can be attached, by its other end to the dental plate. The arm is bent until the arch wire holder is in the correct, desired position. By means of this arm a correction option relating to four degrees of freedom important to orthodontics is obtained:

The bracket holder can be adjusted in the height direction of the tooth, for example to correct a tooth which has sunk too deeply into the jaw or to make a correction for a dental plate which has been stuck to the tooth too low or too high.

The arch wire holder can be tilted round a tilt axis which extends substantially transversely to the longitudinal direction of the tooth and transversely to the direction of extension of the tooth arch. It is thus possible, for example, to correct a tooth which is crooked in respect of the adjacent teeth.

It is possible to swivel the arch wire holder in respect of the longitudinal axis of the tooth, for example to correct a tooth which is twisted in respect of said longitudinal axis.

It is possible to adjust the distance from the arch wire holder to the tooth for the purpose of so-called inset or offset. It is thus possible to correct a tooth which projects too far forwards or backwards from the tooth arch.

It is advantageous according to the invention in this case if the arm is substantially L-shaped. This simplifies adjusting of the position of the arch wire holder in relation to the above-mentioned four degrees of freedom.

It is further advantageous according to the invention if the arm is attached, or can be attached, to the dental plate in a detachable manner. This makes it possible to make the bendable wire material of the arm of such rigidity that unintentional bending of the arm by contact with cutlery during eating, for example, or with a tooth from the opposite jaw is counteracted, while additional bending of the arm when the arm is detached from the bracket is indeed possible. This also prevents unintentional breaking of the adhesive connection between dental plate and tooth taking place while the arm is being additionally bent by the orthodontist.

The detachable fastening of the arm to the dental plate can be advantageously implemented according to the invention if the first end of the arm comprises an insertion section and if the dental plate is fitted at the front with a receiving section with a recess, such as a bore, in which the insertion section can be accommodated for attaching the arm to the dental plate. It is thus possible to insert the insertion section on the arm into the recess in a simple manner.

With a view to simple fixing of the arm to the dental plate, it is advantageous according to the invention in this case if, seen in the longitudinal direction of the insertion section, the recess has a length which is shorter than the insertion section and is open on opposite sides, such that when the insertion section is accommodated in the recess the free far end of the insertion section projects out of the recess and displacement of the insertion section in the longitudinal direction of the recess can be prevented by bending the free far end of the insertion section. Said free far end of the insertion section will advantageously be relatively easy to bend—in other words with relatively little force—in respect of the arm. This can be achieved among other ways by making this free far end thinner than the arm itself in places or over its entire length, for example by narrowing this section by tapering. This thus prevents the dental plate accidentally being detached from the tooth by this bending of the free far end.

It is further advantageous according to the invention in this case if the insertion section and the arm have together a substantially U-shaped form. It thus becomes possible to make the entirety of arm and insertion section such that it fits into a relatively limited surface for the dental plate.

Because the total of insertion section, arm and arch wire holder fits entirely within a surface defined by the dental plate, while this surface is relatively small, it is advantageous according to the invention if the insertion section, the arm and the arch wire holder together have a discontinuous rectangular form.

For the purposes of attaching the arch wire and the arch wire holder it is advantageous according to the invention if the arch wire holder defines a groove in which the arch wire can be accommodated for the guiding thereof. With optimum use of the four previously mentioned degrees of freedom in mind, it is advantageous according to the invention in this case if the longitudinal direction of the groove substantially runs transversely to the second end of the arm.

According to a further advantageous embodiment the arch wire holder comprises a cylindrical body with a flattened longitudinal side in which the groove, which extends in the axial direction of the body, is provided and the arch wire holder further comprises a discontinuous ring of a resilient material, rotatable round the body, which ring has a flattening corresponding to the flattened longitudinal side. Thus in a simple manner an attachment of the arch wire to the arch wire holder, to be locked and unlocked in mechanical manner, is produced. The ring of resilient material can be rotated such that the groove lies behind the discontinuous section of the ring, in order to be able to place the arch wire in the groove. The ring can then be rotated again until the flattening of the ring is lying against the flattened longitudinal side of the body. The resilient properties of the ring in this case effect a kind of bias which prevents unintentional rotation of the ring into an unlocking position.

For the purposes of the rotation of the ring, it is advantageous according to the invention if the ring comprises a gripping element, such as an eye or lip, for gripping the ring by means of an instrument, such as a probe.

According to a further aspect the invention relates to the use of a bracket according to the invention, wherein the bracket is attached to a tooth such that the section of the arm comprising the first end of the arm extends in the longitudinal direction of the arch wire and is turned towards the free far end of said tooth—the co-called occlusal side of the tooth. It is thus achieved that the bracket is less thick on the occlusal side than on the opposite cervical side, which keeps problems with the bite in respect of the opposite dentition to a minimum. This sharply reduces damage to the bracket or detaching thereof.

According to yet another aspect the invention relates to the use of a bracket according to the invention, wherein the dental plate is stuck to the tooth by its back by means of an adhesive, in particular a dental adhesive, and wherein the arm is additionally bent into a desired shape.

It is further advantageous according to the invention in this case if this desired shape is such that the arch wire can be fixed in the arch wire holder as a so-called straight wire.

To prevent unintentional detaching of the tooth from the dental plate it is advantageous according to the invention if the additional bending of the arm is done while the arm is detached from the dental plate and the arm is attached to the dental plate after it has been bent into the desired shape.

For the purposes of readjusting or adjusting the entirety of arch wire and brackets, it is advantageous according to the invention if, after the additional bending, during a following check-up appointment, the arm is detached from the dental plate again, the arm is additionally bent again and the arm is attached to the dental plate again.

It is further advantageous according to the invention if the additional bending is done while the arch wire holder is detached from the arch wire. The orthodontist, dentist or any other person carrying out the treatment thus has more freedom for manipulating the arm with the arch wire holder, without having to trouble the patient too much.

BRIEF DESCRIPTION OF THE SEVERAL VIEWS OF THE DRAWINGS

The present invention will be explained in more detail below with reference to the appended drawings, wherein:

FIG. 3 shows a diagrammatic perspective view of the bracket according to FIGS. 1 and 2, but from another viewing angle, wherein the arch wire holder is shown in an open state;

FIG. 4 shows in four partial figures a diagrammatic reproduction of four degrees of freedom important in orthodontics which the bracket according to the invention has and FIG. 5 shows a diagrammatic, perspective reproduction of a tooth arch fitted with brackets according to the invention with an arch wire.

DETAILED DESCRIPTION OF THE INVENTION

Figure 1:
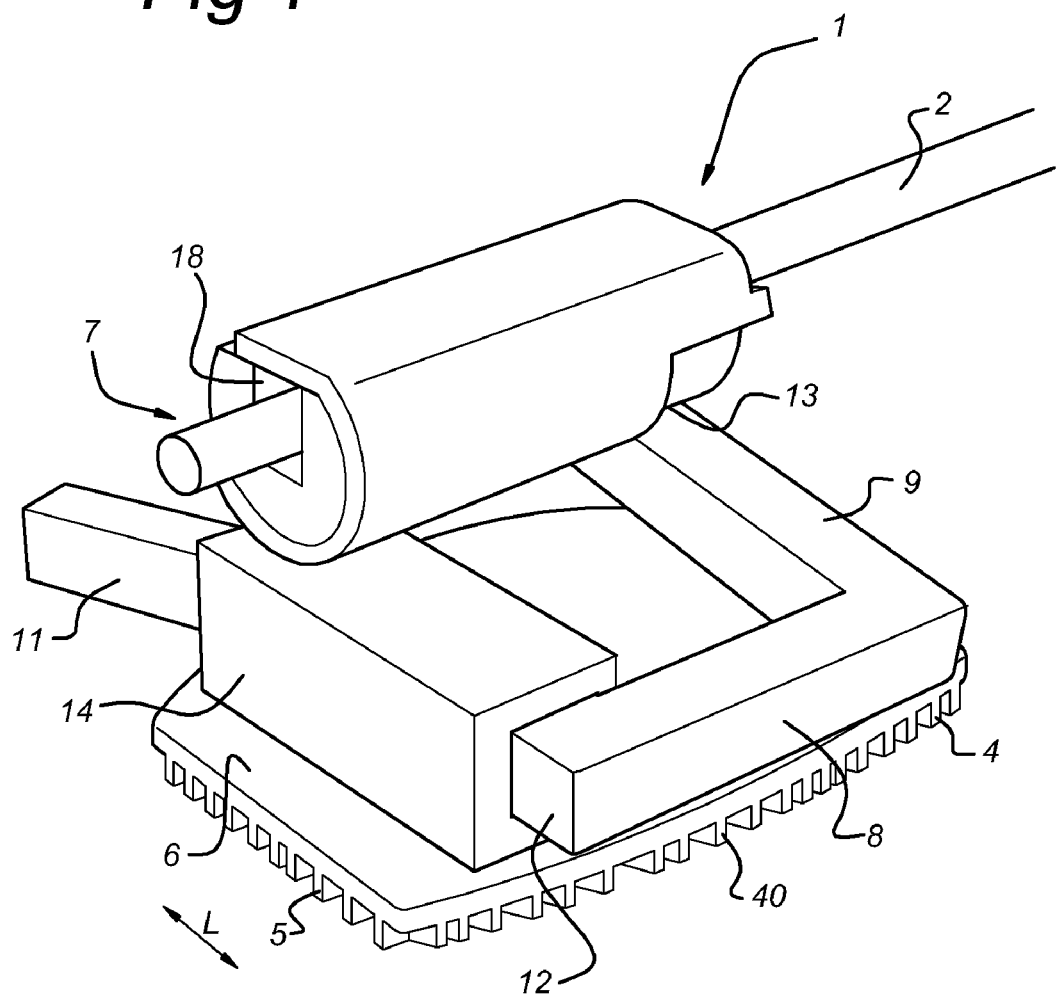
FIG. 1 shows diagrammatically and perspectively a bracket according to the invention.
Figure 2:
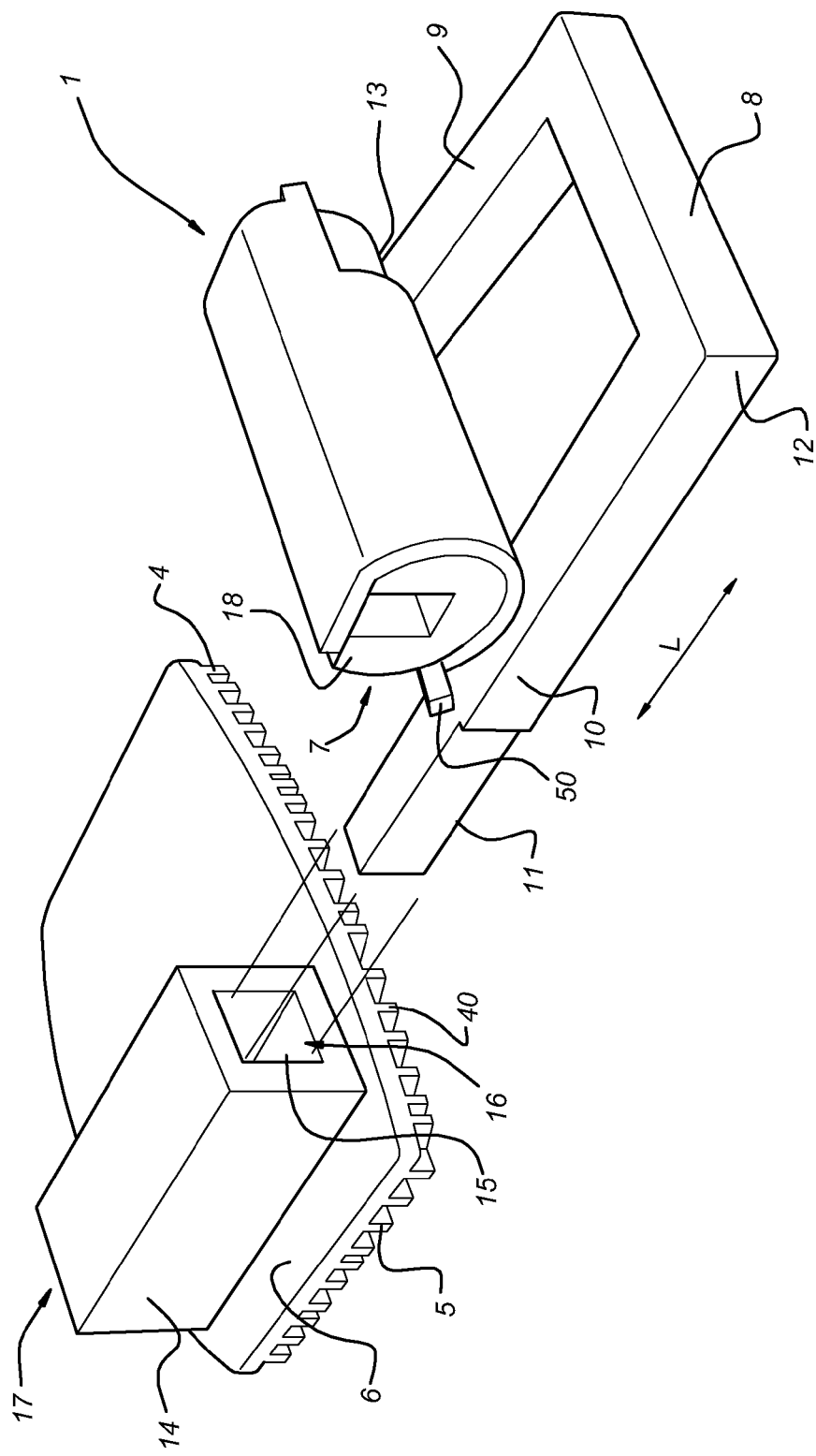
FIG. 2 shows the bracket according to FIG. 1, but now in a state in which the arm of the dental plate has been removed.

With reference to FIGS. 1, 2 and 3, the bracket 1 according to the invention is constructed of a dental plate 4, an arch wire holder 7 and an arm 8, 9.

The dental plate 4 has a back 5, with which the dental plate is to be attached to a tooth by means of an adhesive connection. In order to make the adhesive stick better to the dental plate 4, the dental plate 4 is fitted on the back 5 with a surface constructed from the recess/projections. The dental plate 4 further has a front 6.

The arm 8, 9 extends along the front 6, approximately roughly parallel to the front 6.

An arch wire fixed in the arch wire holder 7 is indicated by 2.

The arch wire holder 7, see in particular also FIG. 3, is constructed from a cylindrical body 19 with a flattened side 20 and a ring 21 fitted round the body 19 with a flattening 22 which corresponds to the flattened side 20 of the body 19. The internal diameter of the ring 21 coincides substantially to the external diameter of the cylindrical body 19. The ring 21 is thus to be rotated round the cylindrical body 19. The flattening 22 prevents unintentional rotation. However, because the ring 21 is made of a resilient material, rotation is quite possible. FIG. 3 shows the ring 21 rotated into a state in which the groove 18 is open in order to be able to place the arch wire 2 therein or to remove it therefrom. FIGS. 1 and 2 show the ring 21 in the closed state, in which the groove 18 is closed off from above. In order to be able to rotate the ring 21 more easily, a gripping element 23, 50 is provided. This gripping element can be made in various ways. It can, for instance, see FIG. 3, be made in the form of an eye 23. The point of a probe simply has to be placed in the eye 23, in order to be able to rotate the ring 21. The gripping element can also, see FIG. 2, be made in the form of a lip 50. The lip 50 can be taken hold of by pliers to be able to rotate the ring 21. This lip 50 is illustrated in FIG. 2 on the side edge, but can also be provided at some other place, for example at the place where the eye 23 is fitted in FIG. 3.

The arm 8, 9 has a first end 12 by which the arm is attached to the dental plate and a second, free end 13 which carries the arch wire holder 7. The arch wire holder 7 is firmly welded to the free end 13 in this case, but attaching can also take place differently.

The arm 8, 9 is an overhanging arm. In the illustrative embodiment shown the arm 8, 9 is L-shaped with a first arm segment 8 and a second arm segment 9. The arm 8, 9 provides on the bracket 1 according to the invention four degrees of freedom important for orthodontics. Because of the L-shaped configuration of the arm 8, 9 controlled bending of the arm 8, 9 for the purposes of correct adjustment is made considerably easier. The four degrees of freedom important for orthodontics are indicated diagrammatically in greater detail in FIG. 4, wherein:

FIG. 4A shows in a diagrammatic way a tooth 3 with a root section 31 and a longitudinal axis 30. The degree of freedom of height adjustability is indicated in this case by the double arrow H, which extends substantially parallel to the longitudinal direction of the tooth 3.

FIG. 4B shows again diagrammatically a tooth 3 with a longitudinal axis 30 and root zone 31. In this tooth a transverse axis, which is perpendicular to the drawing surface and will also be transverse to the arch shape of the tooth arch in the case of a neat tooth arch. In FIG. 4B the so-called tipping degree of freedom is indicated by the double arrow T. This degree of freedom T amounts to tilting of the tooth 3 in the lateral direction round the tilt axis.

FIG. 4C shows the rotation degree of freedom, indicated by R. This is a degree of freedom in which the tooth 3 is rotated round the longitudinal axis 30 thereof.

FIG. 4D shows in top view diagrammatically a tooth arch 33 with teeth standing regularly in the arch shape and two teeth 34 and 35 standing irregularly. Tooth 34 is in a so-called retruded position, in which tooth 34, from outside looking into the mouth, lies sunk as it were behind the tooth arch 3. Tooth 35 shows a so-called protruded position, in which tooth 35, seen from outside looking into the mouth, lies in a position jutting forwards in respect of the tooth arch 33.

The so-called height adjustment can be achieved by bending arm 8 as it were parallel to the dental plate 4 in one direction or the other direction. The groove 18 is in this case to be held aligned on the arch wire 2 by likewise additionally bending arm 9 slightly in a direction substantially parallel to the plane of the dental plate 4.

The tipping degree of freedom is to be used by, for example, just additionally bending arm 8 slightly. The arch wire 2, running straight through, will then be inclined to want to bend the arm 8 back via the arch wire holder 7 and thus to make the tooth 3 tip.

The rotation degree of freedom according to FIG. 4C is to be used by, for example, twisting arm 9 slightly. The arch wire 2 will then be inclined to twist arm 9 back via the arch wire holder. Arm 9 is too rigid for this. As a result a rotational force will be exerted on the tooth 3.

In the case of a retruding tooth 34 according to FIG. 4D it will be possible to pull this tooth back into the tooth arch by positioning the arch wire holder 7 closer to the dental plate 4 than is suitable if the arch wire 2 runs straight through unimpeded. The arch wire will thus be inclined to pull the tooth 34 back into the tooth arch. Correction of the protruding tooth 35 will be able to take place directly in reverse by positioning the arch wire holder 7 in a place slightly too far away from the dental plate 4. However, this can also be achieved in equivalent manner by adjusting the brackets of the laterally adjacent teeth 3 correspondingly, as described in the case of the bracket for tooth 34.

In order to simplify the bending of the arm 8, 9 for the purposes of positioning the arch wire bracket 7 in the desired way, arm 8 is fitted on its first end 12, which is fixed, with an insertion section 10 with a free far end 11. Fitted to the dental plate 4 is a receiving part 14 with a bore 15 through it. The length of the bore 15 is shorter than the length of the insertion section 10 which is inserted along path 16 beyond the end 17. This provides the option of bending the free end 11 of the insertion section slightly and thus preventing unintentional detaching of the insertion section 10 from the receiving part 14 and thus detaching of the arm 8, 9.

With reference to FIGS. 1, 2 and 3, one of the sides of the dental plate is indicated by 40. This side 40 is called the so-called occlusal side, because this side 40 is preferably turned towards the free, occlusal end of the tooth when the bracket is mounted. The occlusal end of the tooth is the end of the tooth where the cutting plane or the chewing plane is provided.

Figure 5:
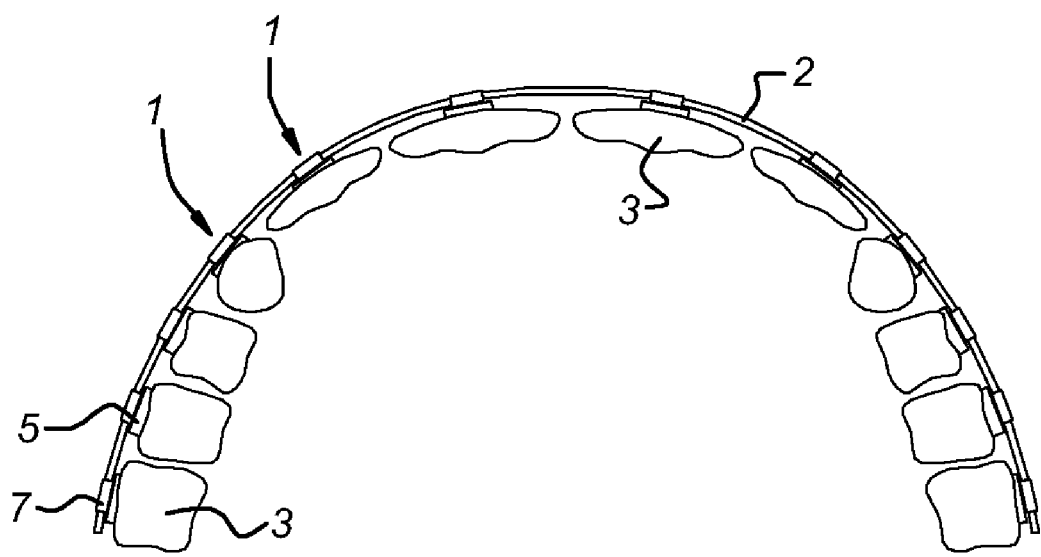

Finally, FIG. 5 shows in a very diagrammatic manner a view of the occlusal side of a tooth arch, wherein the teeth are fitted with brackets according to the invention with which an arch wire 2 is attached to the teeth. This figure is for illustration and has therefore been left very diagrammatic.

The invention claimed is:

1. A bracket for attaching an arch wire to a tooth, wherein the bracket comprises:
    a dental plate with a back and a front, the back is adapted to attach to said tooth by an adhesive connection;
    an arch wire holder for attaching the arch wire to the bracket, the arch wire holder being fitted at the front of the dental plate; and
    an arm, a first end of which is attached to the dental plate, and a second end carries the arch wire holder,
    wherein the arm extends along the front of the dental plate,
    wherein the arm is made of bendable wire material, such that a position of the arch wire holder is adjustable in respect of the dental plate by bending the arm,
    wherein the arm is L-shaped, and the bracket is attachable to said tooth such that a section of the arm, which comprises the first end of the arm, extends in a longitudinal direction of the arch wire and is turned towards an occlusal side of said tooth.

2. The bracket according to claim 1, wherein the arm is attached, or can be attached, to the dental plate in a detachable manner.

3. The bracket according to claim 1, wherein said first end of the arm comprises an insertion section, and
wherein the dental plate is provided at the front with a receiving section with a recess, in which the insertion section accommodates attachment of the arm to the dental plate.

4. The bracket according to claim 3, wherein, seen in the longitudinal direction of the insertion section, the recess has a length which is shorter than the insertion section and is open on opposite sides, wherein upon the insertion section being accommodated in the recess, a free far end of the insertion section projects from the recess and displacement of the insertion section in the longitudinal direction of the recess is to be prevented by bending the free far end of the insertion section.

5. The bracket according to claim 3, wherein the insertion section and the arm together have a U-shaped form.

6. The bracket according to claim 3, wherein the insertion section, the arm and the arch wire holder together have a discontinuous rectangular form.

7. The bracket according to claim 1, wherein the arch wire holder defines a groove for arch wire accommodation.

8. The bracket according to claim 7, wherein the longitudinal direction of the groove runs substantially transversely to the second end of the arm.

9. The bracket according to claim 7,
wherein the arch wire holder comprises a cylindrical body with a flattened longitudinal side in which the groove, which extends in an axial direction of the body, is provided; and
wherein the arch wire holder further comprises a discontinuous ring made of a resilient material, rotatable about the body, which ring has a flattening corresponding to the flattened longitudinal side.

10. The bracket according to claim 9, wherein the ring comprises a gripping element, gripping the ring by an instrument.

11. A method of use of a bracket for attaching an arch wire to a tooth, the bracket comprises a dental plate with a back and a front, the back is adapted to attach to said tooth by an adhesive connection, an arch wire holder attaching the arch wire to the bracket, the arch wire holder being fitted at the front of the dental plate, and an arm, a first end of which is attached to the dental plate, and a second end carries the arch wire holder, the arm extends along the front of the dental plate, the arm is made of bendable wire material, such that a position of the arch wire holder is adjustable in respect of the dental plate by bending the arm, the arm is L-shaped, and the bracket is attached to said tooth such that a section of the arm, which comprises the first end of the arm, extends in a longitudinal direction of the arch wire and is turned towards an occlusal side of said tooth, the method comprising:
adhering the back of the dental plate to said tooth by an adhesive; and
additionally bending the arm into a desired shape.

12. The method according to claim 11, wherein said desired shape is such that the arch wire can be attached in the arch wire holder as a straight wire.

13. The method according to claim 11, wherein the additionally bending of the arm is done while the arm is detached from the dental plate and the arm is attached to the dental plate after being bent into the desired shape.

14. The method according to claim 13, wherein, after the additionally bending, during a following check-up appointment, the arm is detached from the dental plate again, the arm is additionally bent again and the arm is attached to the dental plate again.

15. The method according to claim 11, wherein the additional bending of the arm is done while the arch wire holder is detached from the arch wire.

16. The method use according to claim 11, wherein the adhesive is a dental adhesive.

17. The bracket according to claim 10, wherein the instrument is a probe.

* * * * *